(12) United States Patent
Ehrnsperger et al.

(10) Patent No.: US 9,285,302 B2
(45) Date of Patent: Mar. 15, 2016

(54) METHOD FOR DETERMINING PROPERTIES OF SUPERABSORBENT POLYMER PARTICLES AND OF ABSORBENT STRUCTURES CONTAINING SUCH PARTICLES

(75) Inventors: Bruno Johannes Ehrnsperger, Bad Soden (DE); Marc Jennewein, Taunusstein (DE); Marion Michnacs, Schwalbach/Ts (DE); Andrea Peri, Schwalbach/Ts (DE); Maike Thomann, Kriftel (DE)

(73) Assignee: The Procter & Gamble Company, Cincinnati, OH (US)

( * ) Notice: Subject to any disclaimer, the term of this patent is extended or adjusted under 35 U.S.C. 154(b) by 546 days.

(21) Appl. No.: 13/524,014

(22) Filed: Jun. 15, 2012

(65) Prior Publication Data

US 2012/0318046 A1    Dec. 20, 2012

(30) Foreign Application Priority Data

Jun. 17, 2011   (EP) .................................... 11004977

(51) Int. Cl.
 *G01N 15/08*  (2006.01)
(52) U.S. Cl.
 CPC .................................. *G01N 15/0826* (2013.01)
(58) Field of Classification Search
 CPC . G01N 15/0826; G01N 15/082; G01N 15/08; B01D 65/102
 USPC .......................................................... 73/38
 See application file for complete search history.

(56) References Cited

U.S. PATENT DOCUMENTS

| 4,340,706 | A | | 7/1982 | Obayashi et al. | |
|---|---|---|---|---|---|
| 5,669,894 | A | * | 9/1997 | Goldman et al. | ............. 604/368 |
| 5,849,816 | A | | 12/1998 | Suskind et al. | |
| 6,258,996 | B1 | * | 7/2001 | Goldman | ...................... 604/368 |
| 6,372,952 | B1 | * | 4/2002 | Lash et al. | ..................... 604/369 |
| 7,537,832 | B2 | | 5/2009 | Carlucci et al. | |
| 8,076,530 | B2 | * | 12/2011 | Kamphus et al. | ............. 604/367 |
| 2005/0113772 | A1 | | 5/2005 | LaFortune | |
| 2008/0161499 | A1 | * | 7/2008 | Riegel et al. | ............... 525/326.1 |
| 2008/0187756 | A1 | * | 8/2008 | Riegel et al. | .................. 428/407 |
| 2009/0192035 | A1 | | 7/2009 | Stueven et al. | |
| 2009/0258994 | A1 | | 10/2009 | Stueven et al. | |
| 2010/0068520 | A1 | | 3/2010 | Stueven | |

FOREIGN PATENT DOCUMENTS

| EP | 0640330 | 3/1995 |
|---|---|---|
| WO | WO 99/34841 | 7/1999 |
| WO | WO 99/34842 | 7/1999 |
| WO | WO 2006/083584 | 8/2006 |

OTHER PUBLICATIONS

"Lauryl Alcohol Ethoxylates", Dec. 12, 2011, Retrieved from the Internet: URL:http://chemicalland21.com/specialtychem/perchem/LAURYL%20ALCOHOL%20ETHOXYLATE.htm.
European Search Report, Application No. 11004977.2, dated Feb. 1, 2012, 8 pages.

\* cited by examiner

(Continued)

*Primary Examiner* — John Fitzgerald
*Assistant Examiner* — Rodney T Frank
(74) *Attorney, Agent, or Firm* — Andrew J. Mueller; Andrew A Paul; Richard L. Alexander (57) ABSTRACT

A method for determining the time dependent effective permeability and the uptake kinetics of hydrogel-forming superabsorbent polymer particles under pressure.

20 Claims, 3 Drawing Sheets

METHOD FOR DETERMINING PROPERTIES OF SUPERABSORBENT POLYMER PARTICLES AND OF ABSORBENT STRUCTURES CONTAINING SUCH PARTICLES

FIELD

The present disclosure is directed to test methods for determining liquid uptake properties of superabsorbent polymer particles and of absorbent structures suitable for use in absorbent articles such as disposable diapers, training pants and adult incontinence undergarments.

BACKGROUND

Absorbent articles, such as disposable diapers, training pants, and adult incontinence undergarments, absorb and contain body exudates. Some absorbent articles, like diapers, contain superabsorbent polymer material. Superabsorbent polymers are typically present in an absorbent structure such as the absorbent core of the absorbent articles in the form of particles. Superabsorbent polymer particles are able to absorb liquid and swell when coming into contact with liquid exudates. However, not all categories of superabsorbent polymer particles and of absorbent structures are equally suitable for use in an absorbent article.

It is generally known that in order to have absorbent articles comprising superabsorbent polymer particles which exhibit good absorbing and containing functions, specific technical requirements should be fulfilled by the superabsorbent polymer particles and the absorbent structures in which the superabsorbent polymer particles are contained.

The superabsorbent polymer particles and the absorbent structure should also highly permeable to liquid. A poor permeability of the superabsorbent polymer particles or the structure containing them may induce leakage of the absorbent article due to gel blocking. Gel blocking can occur in the absorbent structure when swelling superabsorbent polymer particles block the void spaces between the particles. In such a case, the liquid exudates cannot or very slowly reach underneath layers of superabsorbent polymer particles disposed in the absorbent structure. The liquid exudates remain on the surface of the absorbent structure and may therefore leak from the diaper.

The permeability of the superabsorbent polymer particles has typically been characterized in the prior art by measuring the SFC (Saline Flow Conductivity) of the particles. This parameter is measured at equilibrium, i.e. the measure is performed on a fully preswollen gel bed of superabsorbent polymer particles.

Similarly, the permeability of absorbent structures has also been characterized in the prior art on fully preswollen absorbent structures.

However, the inventors have now surprisingly found that superabsorbent polymer particles and absorbent structures having a high permeability measured at equilibrium do not automatically result in fast acquisition times of liquid exudates into the absorbent article, especially at the first gush, i.e. when the dry superabsorbent polymer particles first come into contact with liquid (i.e. when the superabsorbent polymer particles are far from reaching equilibrium).

The present disclosure therefore provides a test method to determine the time it takes for dry superabsorbent polymer particles to reach a certain liquid uptake, as well as to determine the dynamic permeability of superabsorbent polymer particles or of absorbent structures containing them. Hence, it is possible to use this method in order to determine the behavior of the superabsorbent polymer particle or of absorbent structures containing them upon their first contact with liquid. The method thus enables an easier selection of the suitable superabsorbent polymer particles or absorbent structures containing them for use in absorbent articles.

SUMMARY

The present disclosure generally relates to a method for determining the time dependent effective permeability and the uptake kinetics of superabsorbent polymer particles under pressure and under condition representative of the structure they are embedded. The method comprises the steps of:

a) providing dry superabsorbent polymer particles on a screen to form a layer or providing an absorbent structure containing superabsorbent polymer particles on a screen, wherein the bottom of the screen has pores, the pores having a dimension to allow liquid to pass through and to hinder the superabsorbent polymer particles from passing through;

b) applying a weight onto the surface of the superabsorbent polymer particles layer or onto the surface of the absorbent structure;

c) introducing a flow of hydrophilic liquid onto the surface of the superabsorbent polymer particles layer or onto the surface of the absorbent structure; and d) measuring and recording the weight of liquid passing through the superabsorbent polymer particles layer or the absorbent structure and the caliper of the superabsorbent polymer particles layer or the absorbent structure.

DETAILED DESCRIPTION

"Absorbent article" is used herein to refer to devices that absorb and contain body exudates, and, more specifically, refers to devices that are placed against or in proximity to the body of the wearer to absorb and contain the various exudates discharged from the body. Absorbent articles include diapers, training pants, adult incontinence undergarments, feminine hygiene products and the like. As used herein, the term "body fluids" or "body exudates" includes, but is not limited to, urine, blood, vaginal discharges, breast milk, sweat and fecal matter. The absorbent article may be a diaper or training pant.

"Absorbent structure" is used herein to refer to a structure disposed between a topsheet and backsheet of an absorbent article for absorbing and containing liquid received by the absorbent article. This structure may comprise one or more substrate layer(s), superabsorbent polymer particles disposed on the one or more substrate layers, and a thermoplastic composition typically disposed on the superabsorbent polymer particles. Typically the thermoplastic composition is a thermoplastic adhesive material. In one embodiment, the thermoplastic adhesive material forms a fibrous layer which is at least partially in contact with the superabsorbent polymer particles on the one or more substrate layers and partially in contact with the one or more substrate layers. In one embodiment, auxiliary adhesive might be deposited on the one or more substrate layers before application of the superabsorbent polymer particles for enhancing adhesion of the superabsorbent polymer particles and/or of the thermoplastic adhesive material to the respective substrate layer(s). The absorbent structure may also include one or more cover layer(s). The one or more substrate layer(s) and the cover layer(s) may comprise or consist of a nonwoven. The absorbent structure may further comprise odor control compounds.

In some embodiments, the absorbent structure would consist essentially of the one or more substrate layer(s), the superabsorbent polymer particles, the thermoplastic composition, optionally the auxiliary adhesive, optionally the cover layer(s), and optionally odor control compounds.

"Airfelt" is used herein to refer to comminuted wood pulp, which is a form of cellulosic fiber.

"Superabsorbent polymer particle" is used herein to refer to cross linked polymeric materials that can absorb at least 10 times their weight of an aqueous 0.9% saline solution as measured using the Centrifuge Retention Capacity test (EDANA WSP 241.2-05). The superabsorbent polymer particles are in particulate form so as to be flowable in the dry state. Example superabsorbent polymer particles of the present disclosure are made of poly(meth)acrylic acid polymers. However, e.g. starch-based superabsorbent polymer particles are also within the scope of the present disclosure.

The Superabsorbent Polymer Particles

The superabsorbent polymer particles useful for the present disclosure may be of numerous shapes. The term "particles" refers to granules, fibers, flakes, spheres, powders, platelets and other shapes and forms known to persons skilled in the art of superabsorbent polymer particles. In some embodiments, the superabsorbent polymer particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and alternatively less than 250 µm down to 50 µm. The length of the fibers may be about 3 mm to about 100 mm. The fibers can also be in the form of a long filament that can be woven.

Alternatively, in some embodiments, superabsorbent polymer particles of the present disclosure are spherical-like particles. According to the present disclosure and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. In such embodiments, the superabsorbent polymer particles may have a particle size of less than 850 µm, or from 50 to 850 µm, alternatively from 100 to 500 µm, and alternatively from 150 to 300 µm, as measured according to EDANA method WSP 220.2-05. Superabsorbent polymer particles having a relatively low particle size help to increase the surface area of the absorbent material which is in contact with liquid exudates and therefore support fast absorption of liquid exudates.

The superabsorbent polymer particles useful in the present disclosure include a variety of water-insoluble, but water-swellable polymers capable of absorbing large quantities of fluids. Such polymers materials are generally known in the art.

Suitable superabsorbent polymer particles may for example be obtained from inverse phase suspension polymerizations as described in U.S. Pat. No. 4,340,706 and U.S. Pat. No. 5,849,816 or from spray- or other gas-phase dispersion polymerizations as described in U.S. Patent Applications No. 2009/0192035, 2009/0258994, 2010/0068520. In some embodiments, suitable superabsorbent polymer particles may be obtained by current state of the art production processes as is more particularly described from page 12, line 23 to page 20, line 27 of WO 2006/083584.

In some embodiments, the surface of the superabsorbent polymer particles may be coated. In such embodiments, the coating makes the surface sticky so that superabsorbent polymer particles cannot rearrange (so they cannot block voids) easily upon wetting.

In some embodiments, the superabsorbent polymer particles may be coated with a cationic polymer. Example cationic polymers can include polyamine or polyimine materials. Example polyamine materials can be selected from the group consisting of (1) polymers having primary amine groups (e.g., polyvinylamine, polyallyl amine); (2) polymers having secondary amine groups (e.g., polyethylenimine); and (3) polymers having tertiary amine groups (e.g., poly N,N-dimethylalkyl amine).

Practical examples of the cationic polymer are, for example, polyethylenimine, a modified polyethylenimine which is crosslinked by epihalohydrin in a range soluble in water, polyamine, a modified polyamidoamine by graft of ethyleneimine, polyetheramine, polyvinylamine, polyalkylamine, polyamidopolyamine, and polyallylamine.

In some embodiments, a cationic polymer has a weight-average molecular weight of at least 500, alternatively 5,000, and alternatively 10,000 or more. Cationic polymers having a weight-average molecular weight of more than 500 or more are not limited to polymers showing a single maximum value (a peak) in a molecular weight analysis by gel permeation chromatography, and polymers having a weight-average molecular weight of 500 or more may be used even if it exhibits a plural maximum value (peaks).

An amount of the cationic polymer may be in a range of from about 0.05 to 20 parts by weight against 100 parts by weight of the superabsorbent polymer particle, alternatively from about 0.3 to 10 parts by weight, and alternatively from about 0.5 to 5 parts by weight.

In some embodiments, the superabsorbent polymer particles may be coated with chitosan materials such as those disclosed in U.S. Pat. No. 7,537,832 B2.

In some other embodiments, the superabsorbent polymer particles may comprise mixed-bed Ion-Exchange absorbent polymers such as those disclosed in WO 99/34841 and WO 99/34842.

Hitherto, absorption properties of dry superabsorbent polymer particles related to the initial uptake has not been investigated. Rather, the focus has been on Saline Flow Conductivity (SFC), which is determined at equilibrium and thus at a stage remote from initial liquid uptake. For absorbent structures of absorbent articles containing a significant amount of airfelt in addition to superabsorbent polymer particles, temporary storage of liquid entering the absorbent structures is provided by the airfelt allowing the superabsorbent polymer particles to absorb liquid from the surrounding airfelt with a certain delay. But even for airfelt free absorbent articles disclosed in the prior art, permeability of the superabsorbent polymer particles has always been measured at equilibrium, thus not taking into account the behavior of dry superabsorbent polymer particles upon initial exposure to liquid.

However, dry superabsorbent polymer particles are typically more reluctant to absorb water than wetted superabsorbent polymer particles. It has been found that the diffusivity of water into dry superabsorbent polymer particles is lower than the diffusivity of water into wetted superabsorbent polymer particles. Therefore, the inventors of the present disclosure have carefully investigated superabsorbent polymer particles behavior upon initial exposure to liquid. They have found that certain, not yet publicly available superabsorbent polymer particles exhibit superior performance when applied in absorbent structures containing no or very low amounts of airfelt. Superior performance of the absorbent structures containing such superabsorbent polymer particles has also been observed. The superior performances of the superabsorbent polymer particles and of the absorbent structures containing them has led to improved liquid acquisition, thus reducing the risk of leakage of absorbent articles in which the superabsorbent polymer particles or the absorbent structure containing them have been incorporated. It has been found that superior superabsorbent polymer particles or superior absorbent structures containing them can be described in terms of the time it takes for dry superabsorbent polymer particles or absorbent structures containing them to reach a certain liquid uptake. Thereby, it is now possible to purposefully and easily select these newly developed superabsorbent polymer particles or absorbent structures containing them, which are specifically suitable for use in absorbent articles comprising little or no airfelt, without the need for additional extensive investigation and testing Superabsorbent polymer particles and absorbent structures containing them are especially useful in absorbent articles such as disposable diapers.

K(t) Test Method (Dynamic Effective Permeability and Uptake Kinetics Measurement Test Method)

This method determines the time dependent effective permeability (K(t)) and the uptake kinetics of a gel layer formed from hydrogel-forming superabsorbent polymer particles or of an absorbent structure containing such particles under a confining pressure. The objective of this method is to assess the ability of the gel layer formed from hydrogel-forming superabsorbent polymer particles or the absorbent structure containing them to acquire and distribute body fluids when the polymer is present at high concentrations in an absorbent article and exposed to mechanical pressures as they typically occur during use of the absorbent article. Darcy's law and steady-state flow methods are used to calculate effective permeability (see below). (See also for example, "Absorbency," ed. by P. K. Chatterjee, Elsevier, 1982, Pages 42-43 and "Chemical Engineering Vol. II, Third Edition, J. M. Coulson and J. F. Richardson, Pergamon Press, 1978, Pages 122-127.)

In contrast to previously published methods, the sample is not preswollen therefore the hydrogel is not formed by preswelling hydrogel-forming superabsorbent polymer particles in synthetic urine, but the measurement is started with a dry structure. The equipment used for this method is called 'Zeitabhängiger Durchlässigkeitsprüfstand' or 'Time Dependent Permeability Tester', Equipment No. 03-080578 and is commercially available at BRAUN GmbH, Frankfurter Str. 145, 61476 Kronberg, Germany and is described below. Upon request, operating instructions, wiring diagrams and detailed technical drawings are also available.

Dynamic Effective Permeability and Uptake Kinetic Measurement System

Figure 1:
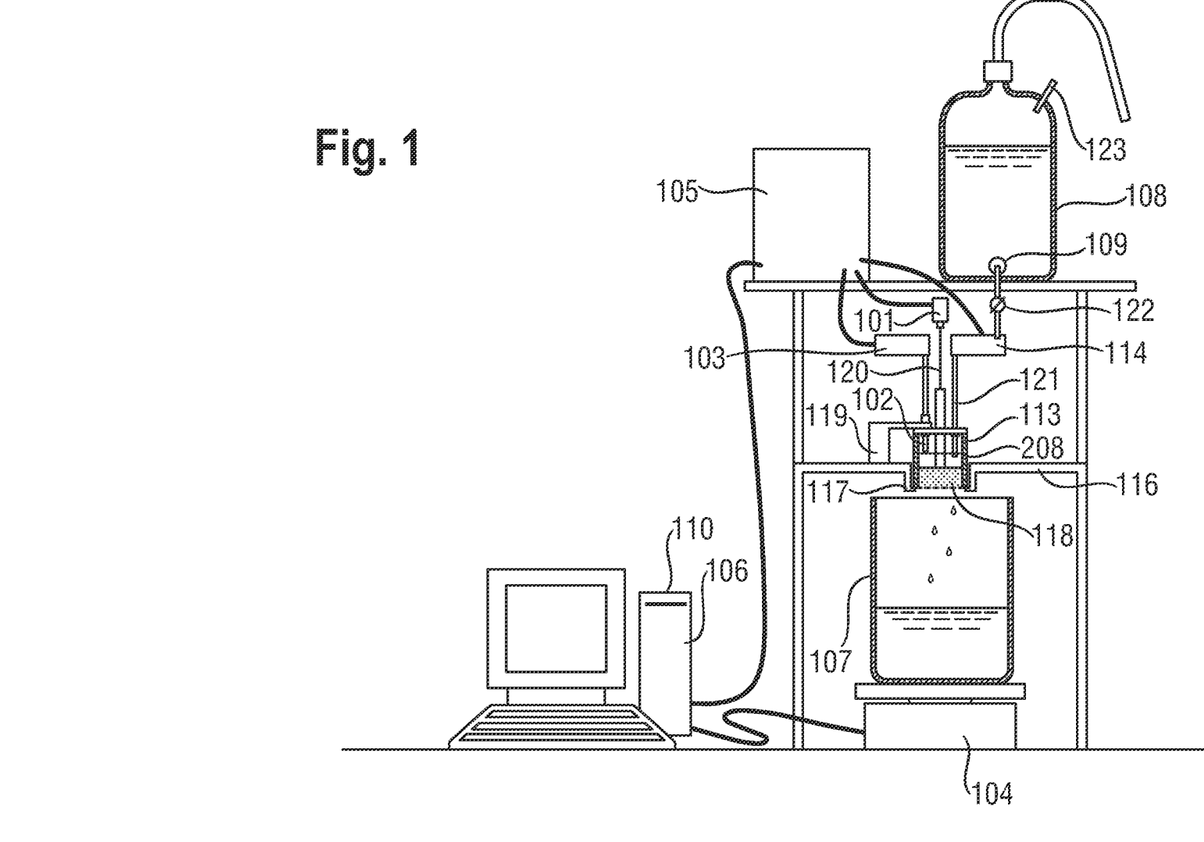
FIG. 1 is a partial cross-sectional side view of a suitable permeability measurement system for conducting the Dynamic Effective Permeability and Uptake Kinetics Measurement Test.

FIG. 1 shows the dynamic effective permeability and uptake kinetic measurement system, called 'Time Dependent Permeability Tester' herein.

The equipment consists of the following main parts:
M11 Digital Laser Sensor for caliper measurement 101 (MEL Mikroelektronik GmbH, 85386 Eching, Germany)
Fiber for Liquid Level Detection 102 (FU95, Keyence Corp., Japan)
Digital Fiber Sensor 103 (FS-N10, Keyence Corp., Japan)
Precision Balance 104 (XP6002MDR, Mettler Toledo AG, 8606 Greifensee, Switzerland)
Power Unit Logo!Power (C98130-A7560-A1-5-7519, Siemens AG)
Labview Software License 106 (National Instruments, Austin, Tx, USA)
Receiving Vessel 107 (5 L Glass Beaker, Roth)
Reservoir 108 (5 L Glass bottle, VWR) with joint 109 and open-end tube for air admittance 123
Operating unit and console 105 (Conrad Electronics)
Computerized data acquisition system 110
A piston/cylinder assembly 113 as described herein
A controlled valve 114 (Bürkert)

Figure 2:
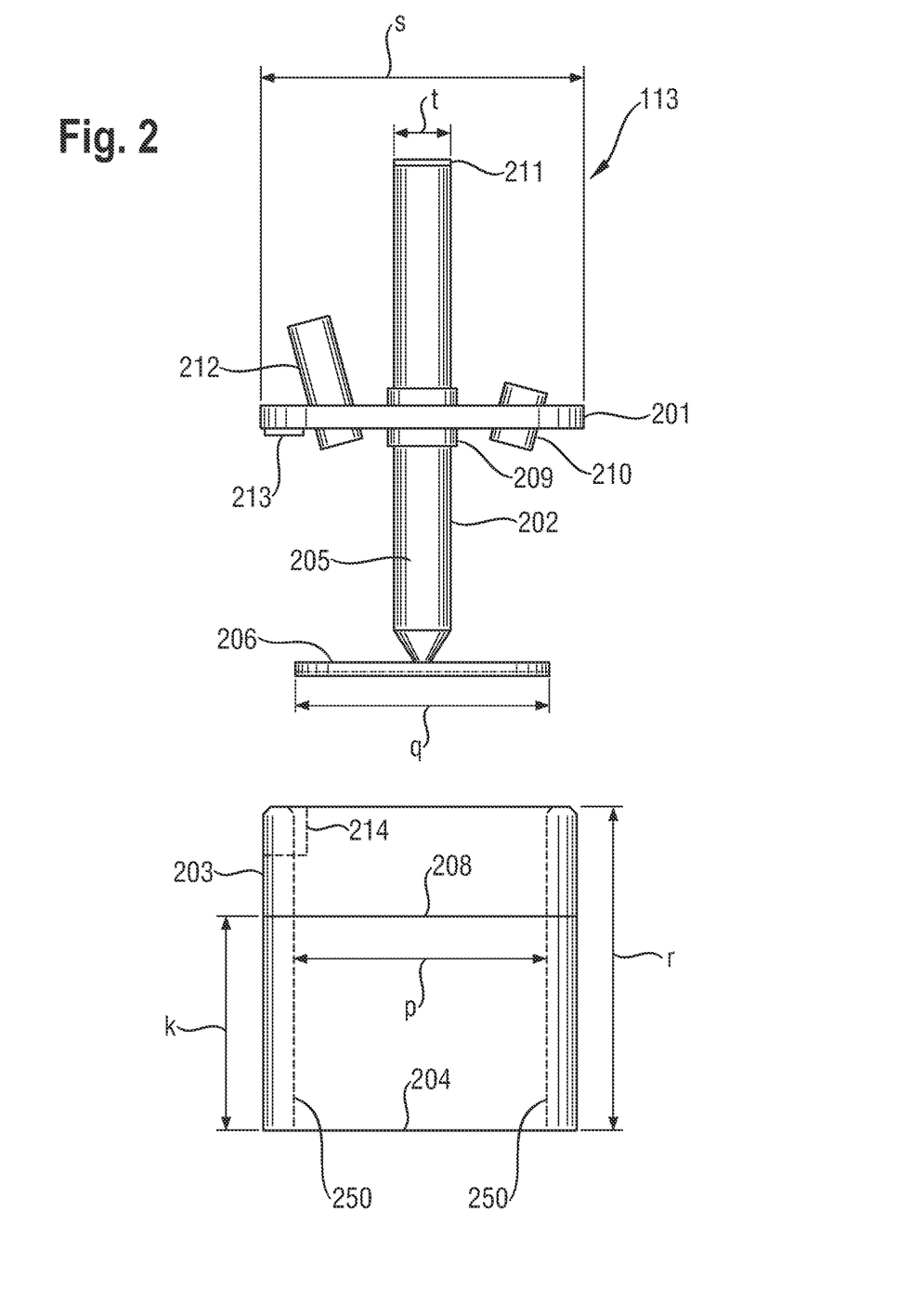
FIG. 2 is a cross-sectional side view of a piston/cylinder assembly for use in conducting the Dynamic Effective Permeability and Uptake Kinetics Measurement Test.
Figure 3:
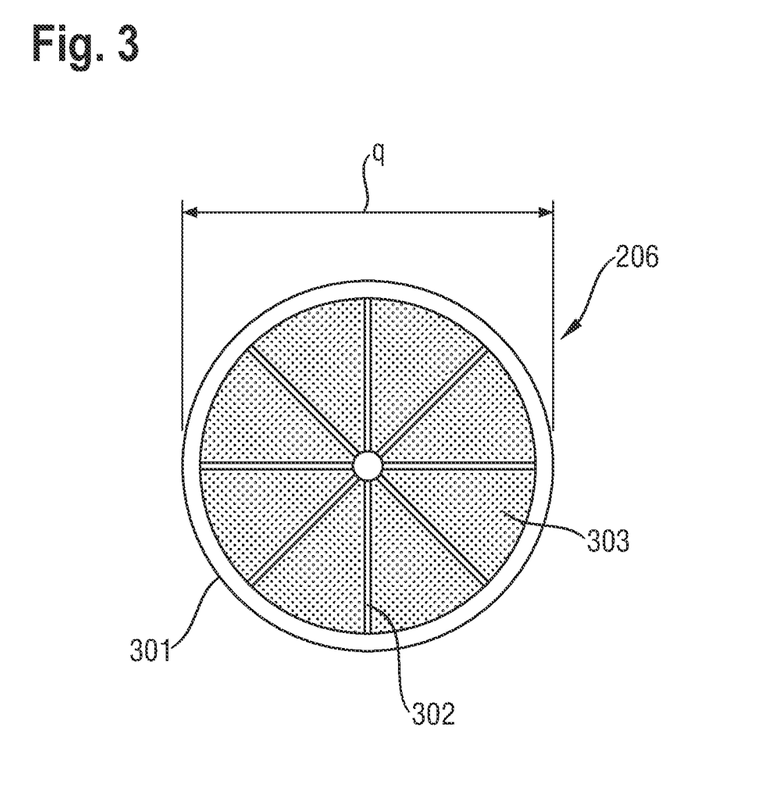
FIG. 3 is a top view of a piston head suitable for use in the piston/cylinder assembly shown in FIG. 2.

FIG. 2 shows the piston/cylinder assembly 113 comprising piston guiding lid 201, piston 202 and cylinder 203. The cylinder 203 is made of transparent polycarbonate (e.g., Lexan®) and has an inner diameter p of 6.00 cm (area=28.27 $cm^2$). The inner cylinder walls 250 are smooth; the height of the cylinder r is about 7.50 cm. The bottom 204 of the cylinder 203 is faced with a US. Standard 400 mesh stainless-steel screen cloth (not shown) (e.g. from Weisse and Eschrich) that is bi-axially stretched to tautness prior to attachment to the bottom 204 of the cylinder 203. The piston 202 is composed of a stainless steel piston body 205 and a stainless steel head 206. The piston head 206 diameter q is slightly less than 6 cm so as to slide freely into the cylinder 203 without leaving any gap for the hydrogel-forming particle to pass trough. The piston body 205 is firmly attached perpendicularly at the center of the piston head 206. The piston body diameter t is about 2.2 cm. The piston body 205 is then inserted into a piston guiding lid 201. The guiding lid 201 has a POM (Polyoxymethylene) ring 209 with a diameter allowing a free sliding of the piston 202 yet keeping the piston body 205 perfectly vertical and parallel to the cylinder walls 250 once the piston 202 with the guiding lid 201 are positioned on top of the cylinder 203. The top view of the piston head 206 is shown in FIG. 3. The piston head 206 is meant to apply the pressure homogeneously to the sample 118. It is also highly permeable to the hydrophilic liquid so as to not limit the liquid flow during measurement. The piston head 206 is composed of a U.S. standard 400 mesh stainless steel screen cloth 303 (e.g. from Weisse and Eschrich) that is bi-axially stretched to tautness and secured at the piston head stainless steel outer ring 301. The entire bottom surface of the piston is flat. Structural integrity and resistance to bending of the mesh screen is. then ensured by the stainless steel radial spokes 302. The height of the piston body 205 is selected such that the weight of the piston 202 composed of the piston body 205 and the piston head 206 is 596 g (±6 g), this corresponds to 0.30 psi over the area of the cylinder 203.

The piston guiding lid 201 is a flat circle of stainless steel with a diameter s of about 7.5 cm held perpendicular to the piston body 205 by the POM ring 209 in its center. There are two inlets in the guiding lid (210 and 212).

The first inlet 212, allows the Fiber for Liquid Level Detection 102 to be positioned exactly 5 cm above the top surface of the screen (not shown) attached to the bottom (204) of the cylinder 203 once the piston 202 is assembled with the cylinder 203 for the measurement.

The second inlet 210 allows connecting a liquid tube 121 providing the liquid to the experiment.

To make sure that the assembly of the piston 202 with the cylinder 203 is done consistently a slit 214 is made on the cylinder 203 matching a position marker 213 in the guiding lid 201. In this way the rotation angle of the cylinder and the guiding lid is always the same.

Prior to every use, the stainless steel screen cloth 303 of the piston head 206 and cylinder 203 should be inspected for clogging, holes or over-stretching and replaced when necessary. A K(t) apparatus with damaged screen can deliver erroneous K(t) and uptake kinetic results, and must not be used until the screen has been replaced.

A 5 cm mark 208 is scribed on the cylinder at a height k of 5.00 cm (±0.02 cm) above the top surface of the screen attached to the bottom 204 of the cylinder 203. This marks the fluid level to be maintained during the analysis. The Fiber for Liquid Level Detection 102 is positioned exactly at the 5 cm mark 208. Maintenance of correct and constant fluid level (hydrostatic pressure) is critical for measurement accuracy A reservoir 108 connected via tubing to the piston/cylinder assembly 113 holding the sample and a controller valve 114 are used to deliver salt solution to the cylinder 203 and to maintain the level of salt solution at a height k of 5.00 cm above the top surface of screen attached to the bottom of the cylinder 204. The valve 114, the Fiber for Liquid Level Detection 102 and the Digital Fiber Sensor 103 are connected to the computerized acquisition system 110 trough the operating unit 105. This allows the Dynamic Effective Permeability and Uptake Kinetic Measurement System to use the information from the Fiber for Liquid Level Detection 102 and the Digital Fiber Sensor 103 to control the valve 114 and ultimately maintain the level of the liquid at the 5 cm mark 208.

The reservoir 108 is placed above the piston/cylinder assembly 113 in such a manner as to allow a 5 cm hydrohead to be formed within 15 seconds of initiating the test, and to be maintained in the cylinder throughout the test procedure. The piston/cylinder assembly 113 is positioned on the support ring 117 of the cover plate 116 and the first inlet 212 is held in place with the docking support 119. This allows only one position of the guiding lid 201. Furthermore, due to the position marker 213, there is also only one position for the cylinder 203. The screen attached to the bottom of the cylinder 204 must be perfectly level and horizontal. The supporting ring 117 needs to have an internal diameter small enough, so to firmly support cylinder 203 but larger than 6.0 cm so to lay outside of the internal diameter of the cylinder once the cylinder is positioned on the supporting ring 117. This is important so to avoid any interference of the supporting ring 117 with the liquid flow.

The salt solution, applied to the sample 118 with a constant hydrohead of 5 cm can now freely flow from the piston/cylinder assembly 113 into a receiving vessel 107 positioned on the balance 104 which is accurate within ±0.01 g. The digital output of the balance is connected to a computerized data acquiition system.

The caliper (thickness) of the sample is constantly measured with a Digital Laser Sensor for caliper measurement 101. The laser beam 120 of the digital laser sensor 101 is directed at the center of the POM cover plate 211 of the piston body. The accurate positioning of all the parts of the piston/cylinder assembly 113 allows the piston body 205 to be perfectly parallel to the laser beam 120 and as a result an accurate measure of the thickness is obtained.

Test Preparation

The reservoir 108 is filled with test solution. The test solution is an aqueous solution containing 9.00 grams of sodium chloride and 1.00 grams of surfactant per liter of solution. The preparation of the test solution is described below. The receiving vessel 107 is placed on the balance 104 which is connected to a computerized data acquisition system 110. Before the start of the measurement the balance is reset to zero.

Preparation of Test Liquid:

Chemicals needed:

Sodium Chloride (CAS#7647-14-5, e.g.: Merck, cat#1.06404.1000)

Linear $C_{12}$-$C_{14}$ alcohol ethoxylate (CAS#68439-50-9, e.g. Lorodac®, Sasol, Italy)

Deionized $H_2O$

Ten liters of a solution containing 9.00 grams per liter of NaCl and 1.00 grams per liter linear $C_{12}$-$C_{14}$ alcohol ethoxylate in distilled water is prepared and equilibrated at 23° C.±1° C. for 1 hour. The surface tension is measured on 3 individual aliquots and should be 28±0.5 mN/m. If the surface tension of the solution is different from 28±0.5 mN/m, the solution is discarded and a new test solution is prepared. The test solution has to be used within 36 hours from its preparation and is considered expired afterwards.

K(t) Sample Preparation

K(t) Test Method can be used to measure superabsorbent polymer particles or an absorbent structure containing such particles, despite the sample preparation being different the two classes of materials, the measuring procedure is identical.

Sample Preparation for Superabsorbent Polymer Particles:

A 10 grams representative sample of the superabsorbent polymer particles is obtained. This is then dried in an uncovered 10 cm diameter Petri dish in a vacuum chamber at 23±2° C. and 0.01 Torr or lower for 48 hours prior to use. The sample is removed from the vacuum chamber and immediately stored in a tightly sealed 20 mL glass airtight container at 23±2° C. until further use.

2.0 g (±0.02 g) of superabsorbent polymer particles are weighed onto a suitable weighing paper using an analytical balance and transferred to the cylinder 203 with the particles distributed evenly on the screen (not shown) attached to the bottom 204 of the cylinder 203. This is done via sprinkling the superabsorbent polymer, while at the same time turning the cylinder clockwise (e.g. on a circular turning table schuett petriturn-M available at Schuett-biotec GmbH, Rudolf-Wissell-Str. 13 D-37079 Göttingen Germany). An even distribution of the superabsorbent polymer particles is critical for the measurements accuracy.

Sample Preparation for Absorbent Structures Containing Superabsorbent Particles:

A representative, undamaged circular portion of the absorbent structure of 6.00 cm diameter is obtained. The portion of the absorbent article can be obtained with a suitable circular die and an hydraulic press cutter (like e.g. Electro-Hydraulic Alfa Cutter 240-10 available at Thwing-Albert instrument company, 14 W. Collings Ave. West Berlin, N.J. 08091). The sample can be obtained from the absorbent structure in any suitable position that might change according to the specific scope of the measurement.

The circular sample 118 is carefully positioned flat on the screen (not shown) attached to the bottom 204 of the cylinder 203 occupying all the available surface on the screen. It is important to position the circular sample 118 in a way that the side in direct contact with the screen is the one that in use is usually more distant form the liquid source so as to reproduce the common flow direction in use. For example for samples related to absorbent article such as diapers, the side usually facing the wearer should be positioned on top while the side facing the garments should be positioned in contact with the screen at the bottom of the cylinder. A careful positioning of the sample is critical for the measurement's accuracy. In case the dimension of the absorbent structure is small and a 6.0 cm diameter sample cannot be obtained from it, it is possible to join two absorbent structures of equal size so to reach the minimum sample size necessary. The two samples need to be taken in an equivalent position from two identical absorbent structures. The two absorbent structures should be joined trough a straight edge and if necessary cut to obtain such a straight edge. The intent is that the joined edges recreate a flat homogeneous layer without any gap. This joint layer is then handled according the standard sample preparation described above with the additional precaution to center the join line in the cutting die so to obtain two half circles of identical shape. It is clearly important that both the half circles are carefully positioned inside the sample holder so to recreate a full circle and occupying the entire available surface on the screen without gaps. Both the halves have to be positioned with the right side facing the screen as explained above.

K(t) Procedure

The measurement is carried out at Tappi lab conditions: 23° C.±1° C./50% RH±2%.

The empty piston/cylinder assembly 113 is mounted in the circular opening in the cover plate 116 and is supported around its lower perimeter by the supporting ring 117. The piston/cylinder assembly 113 is held in place with the docking support 119 with the cylinder 203 and piston 202 aligned at the proper angle. The reference caliper reading ($r_r$) is measured by Digital Laser sensor. After this, the empty piston/cylinder assembly 113 is removed from the cover plate 116 and supporting ring 117 and the piston 202 is removed from the cylinder 203.

The sample 118 is positioned (absorbent structure) or sprinkled (superabsorbent polymer particles) on the cylinder screen as explained above. After this, the piston 202 assembled with the guiding lid 201 is carefully set into the cylinder 203 by matching the position marker 213 of the guiding lid 201 with the slit 214 made in the cylinder 203

The piston/cylinder assembly is held in place with the docking support 119 with the cylinder and piston aligned at the proper angle This can be only done in one way. The liquid tube 121 connected to the reservoir 108 and the Digital Fiber Sensor 103 are inserted into the piston/cylinder assembly 113 via the two inlets 210 and 212 in the guiding lid 201.

The computerized data acquisition system 110 is connected to the balance 104 and to the digital laser sensor for caliper measurement 101. Fluid flow from the reservoir 108 to the cylinder 203 is initiated by the computer program by opening valve 114. The cylinder is filled until the 5 cm mark 208 is reached in 5 to 15 seconds, after which the computer program regulates the flow rate to maintain a constant 5 cm hydrohead. The quantity of solution passing through the sample 118 is measured by the balance 104 and the caliper increase is measured by the laser caliper gauge. Data acquisition is started when the fluid flow is initiated specifically when the valve 114 is opened for the first time, and continues for 21 minutes or until the reservoir runs dry so that the 5 cm hydrohead is no longer maintained. The duration of one measurement is 21 min, laser caliper and balance readings are recorded regularly with an interval that may vary according to the measurement scope from 2 to 10 sec, and 3 replicates are measured.

After 21 min, the measurement of the 1$^{st}$ replicate is successfully completed and the controlled valve 114 closes automatically. The piston/cylinder assembly 113 is removed and the measurements of the 2$^{nd}$ and 3$^{rd}$ replicates are done accordingly, always following the same procedure. At the end of the measurement of the 3$^{rd}$ replicate, the controlled valve 114 stops the flow of liquid and stopcock 122 of the reservoir 108 is closed. The collected raw data is stored in the form of a simple data table, which then can be imported easily to a program for further analysis e.g. Excel 2003, SP3.

In the data table the following relevant information is reported for each reading:

Time from the beginning of the experiment

Weight of the liquid collected by the receiving vessel 107 on the balance 104

Caliper of the sample 118

The data from 30 seconds to the end of the experiment are used in the K(t) and uptake kinetics calculation. The data collected in the first 30 seconds are not included in the calculation. The effective permeability K(t) and the uptake kinetics of the absorbent structure are then determined using the equation sets below.

Used Equations:

The table below describes the notation used in the equations.

| | |
|---|---|
| A | x-section of the absorbent structure sample which corresponds to the cylinder inner radius: 28.27 cm$^2$ |
| h | height of water column, 5.0 cm |
| Δp | driving pressure applied by the 5.00 cm hydrohead (h): 4929.31 g/(cm s$^2$) |
| G | gravity constant: 981 cm/s$^2$ |
| η | Temperature dependent effective viscosity of the liquid in g/(cm s) |
| T | Temperature in ° C. |
| ρ | density of the liquid: 1.0053 g/cm$^3$ |
| $ρ_s^A$ | Apparent sample density of the porous medium or powder in g/cm$^3$ |
| $ρ_s$ | Average density of the solid part of the dry sample in g/cm$^3$ |
| $ρ_{s\,k}$ | Density of the component k of the dry sample in g/cm$^3$ |
| M | dry mass of the sample in g: 2.00 g if measuring superabsorbent particles |
| $m_k$ | Mass of the component k of the dry sample in g |
| $V_s$ | Dry sample volume in cm$^3$ |
| $t_i$ | time at step i of N discrete points in s |
| $d_i$ | caliper of the absorbent structure sample at time $t_i$ in cm |
| $r_i$ | reading of caliper instrument at time $t_i$ in cm |
| $r_r$ | reference reading of caliper instrument (reading of the piston/cylinder assembly without sample) in cm |
| $m_{out\,i}$ | balance reading at time $t_i$; mass of the liquid that left the sample at time $t_i$ in g |
| $U(t_i)$ | Sample uptake at time $t_i$ in g |
| T20 | time required to reach an uptake of 20 g/g, starting at 0 s ($t_0$) in s |
| U20 | Sample uptake after 20 minutes in g/g |
| T80% | Time required to reach an uptake of 80% of U20 starting at 0 s ($t_0$) in s |
| K20 | Sample permeability at 20 minutes in m$^2$ |
| Kmin | the minimum value of the permeability during the experiment in m$^2$ |
| Kmin/K20 | the ratio of Kmin and K20 |

The driving pressure is calculated from the hydro head as follows:

$$\Delta p = h \cdot G \cdot \rho = 4929.31 \text{ g/(cm·s}^2)$$

The caliper at each time $t_i$ is calculated as the difference of the caliper sensor reading at time $t_i$ and the reference reading without sample:

$$d_i = r_i - r_r \quad [\text{cm}]$$

For superabsorbent particles samples the caliper of the sample at time $t_i = 0$ ($d_o$) is used to evaluate the quality of the particle sprinkling.

An apparent sample density inside the cylinder can be in fact calculated as:

$$\rho_s^A = \frac{m}{d_0 \cdot A} \ [\text{g/cm}^3]$$

If this apparent density inside the cylinder differs from the apparent density of the powder by more than ±40% the measurement has to be considered invalid and eliminated.

The apparent density can be measured according EDANA method 406.2-02 ("Superabsorbent materials—Polyacrylate superabsorbent powders—GRAVIMETRIC DETERMINATION OF DENSITY")

The rate of change with time of the balance reading at time $t_i$ is calculated as follows:

$$\frac{dm_{out}(t_i)}{dt} = \frac{m_{out_{i+1}} - m_{out_{i-1}}}{t_{i+1} - t_{i-1}} \ [\text{g/sec}]$$

The rate of change with time of the caliper reading at time $t_i$ is calculated as follows:

$$\frac{dd(t_i)}{dt} = \frac{d_{i+1} - d_{i-1}}{t_{i+1} - t_{i-1}} \ [\text{cm/sec}]$$

The uptake Kinetics is calculated as follows:

$$U(t_i) = \frac{(A \cdot d_i - V_S) \cdot \rho}{m} \ [\text{g/g}]$$

By dry sample volume ($V_s$) is intended the skeletal volume of the sample therefore $V_s$ is the actual volume occupied by the solid material in the dry sample excluding pores and interstitials that might be present.

$V_s$ can be calculated or measured by different methods known by the skilled person for example, knowing the exact composition and the skeletal density of the components it can be determined as follows:

$$V_S = \sum_k V_k = \sum_k \frac{m_k}{\rho_{Sk}} \ [\text{cm}^3]$$

Alternatively for an unknown material composition $V_s$ can be easily calculated as follow:

$$V_S = \frac{m}{\rho_S} \ [\text{cm}^3]$$

The average density $\rho_s$ can be determined by pycnometry with a suitable non-swelling liquid of known density. This technique cannot be performed on the same samples subsequently used for the K(t) measure therefore a suitable additional representative set of samples should be prepared for this experiment measurement.

From U(t) at the different time steps calculated as explained above, one can determine the uptake at any specific time by linear interpolation. For example one of the important outputs is the uptake at 20 minutes also called U20 (in g/g).

From U(t) at the different time steps one can also determine the time required to reach a certain uptake by linear interpolation. The time where the uptake of 20 g/g is first reached is called T20. Similarly the time to reach any other uptakes can be calculated accordingly (e,g T5 or T10). Knowing U20 it is possible to determine from U(t) at the different time steps also the time to reach 80% of U20, this property is called T80%.

The Effective Permeability is calculated as follows from the rates of mass change and caliper change:

$$K(t_i) = \eta \frac{d_i}{\Delta p} \cdot \left( \frac{1}{\rho \cdot A} \cdot \frac{dm_{out}(t_i)}{dt} + \frac{dd(t_i)}{dt} \right) \ [\text{cm}^2]$$

The effective viscosity of the liquid depends on the temperature and in the interval of the experiment (23° C.±1° C.) is calculated according the following empirical equation:

$$\eta = -2.36 \cdot 10^{-4} \cdot T + 1.479 \cdot 10^{-2} [\text{g/(cm s)}]$$

From $K(t_i)$ one can determine the effective permeability at a certain time by linear interpolation. For example one of the important outputs is the uptake at 20 minutes or K20 ($m^2$). Similarly the Permeability at any other time can be calculated accordingly (e.g. K5 or K10).

Another parameter to be derived from the data is Kmin, which is the minimum K(t) value measured over the whole curve in the interval from $t_i=30$ s to $t_i=1200$ s. This value is useful to calculate Kmin/K20 which is the ratio between the minimum effective permeability and the permeability at 20 minutes. This parameter express the temporary gel blocking that might occur in some of the samples. If the value is close to 1 there is no temporary gel blocking if the value is close to 0 it is an indication that the material goes through a strong effective permeability drop when initially loaded with liquid.

The average values for T20, T80%, K20, U20 and Kmin/K20 are reported from 3 replicates according to the accuracy required as known by the skilled man.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining the time dependent effective permeability and the uptake kinetics under pressure of superabsorbent polymer particles or an absorbent structure comprising superabsorbent polymer particles, the method comprising the steps of:
   a. providing dry, non-preswollen, non pre-wetted superabsorbent polymer particles on a screen to form a layer on the screen, wherein the bottom of the screen has pores, the pores having a dimension to allow liquid to pass through and to hinder the superabsorbent polymer particles from passing through;
   b. applying a weight onto the surface of the superabsorbent polymer particles layer;
   c. introducing a flow of hydrophilic liquid onto the surface of the superabsorbent polymer particles layer; and
   d. measuring and recording the weight of liquid passing through the superabsorbent polymer particles layer and the caliper of the superabsorbent polymer particles layer.

2. The method according to claim 1, wherein the weight applies a predetermined, constant and even pressure on the surface of the superabsorbent polymer particles layer or the surface of the absorbent structure.

3. The method according to claim 2, wherein the pressure applied on the surface of the superabsorbent polymer particles layer or on the surface of the absorbent structure is 0.2 psi to 0.4 psi.

4. The method according to claim 1, wherein the screen is attached to the bottom of a cylinder.

5. The method according to claim 1, wherein the superabsorbent polymer particles are evenly dispersed on the screen to form a homogeneous layer.

6. The method according to claim 1, wherein the hydrophilic liquid is a salt solution and is aqueous 0.9% by weight sodium chloride solution.

7. The method according to claim 6, wherein the solution comprises 0.01% by weight of a non-ionic surfactant.

8. The method according to claim 7, wherein the non-ionic surfactant is a linear $C_{12}$-$C_{14}$ alcohol ethoxylate.

9. The method according to claim 1, wherein the amount of the superabsorbent polymer particles provided on the screen or contained in the absorbent structure is predetermined and is about 2.0 g.

10. The method according to claim 1, wherein the liquid is maintained at a constant level in the cylinder at about 5.0 cm.

11. The method according to claim 10, wherein a reservoir is used to deliver the hydrophilic liquid to the cylinder and a digital fiber sensor connected to a controlled valve are used to temporarily block the flux of liquid flowing from the reservoir to the cylinder in order to maintain constant the level of hydrophilic liquid in the cylinder.

12. The method according to claim 1, wherein weight is applied onto the surface of the superabsorbent polymer particles layer or the surface of the absorbent structure by using a piston, the piston comprising a piston body, a piston head and a piston guiding lid, the piston head being positioned onto the surface of the superabsorbent polymer particles layer or the surface of the absorbent structure.

13. The method according to claim 12, wherein the caliper of the superabsorbent polymer particles layer or of the absorbent structure is measured by a digital laser sensor which is pointed at the top of the piston body.

14. The method according to claim 13, wherein the piston guiding lid comprises an inlet, and wherein the hydrophilic liquid is introduced in the cylinder via the outlet of a liquid tube connected to the reservoir, the liquid tube being inserted into the cylinder via the inlet of the piston guiding lid.

15. The method according to claim 1, wherein the amount of hydrophilic liquid passing through the superabsorbent polymer particles layer or the absorbent structure and the caliper of the superabsorbent polymer particles layer or the absorbent structure are recorded for a period of at least 21 minutes.

16. A method for determining the time dependent effective permeability and the uptake kinetics under pressure of an absorbent structure comprising superabsorbent polymer particles, the method comprising the steps of:
   a. providing an absorbent structure comprising dry, non-preswollen, non pre-wetted superabsorbent polymer particles on a screen, wherein the bottom of the screen has pores, the pores having a dimension to allow liquid to pass through and to hinder the superabsorbent polymer particles from passing through;
   b. applying a weight onto the surface of the absorbent structure;
   c. introducing a flow of hydrophilic liquid onto the surface of the absorbent structure; and
   d. measuring and recording the weight of liquid passing through the absorbent structure and the caliper of the absorbent structure.

17. The method according to claim 16, wherein the weight applies a predetermined, constant and even pressure on the surface of the absorbent structure.

18. The method according to claim 17, wherein the pressure applied on the surface of the absorbent structure is 0.2 psi to 0.4 psi.

19. The method according to claim 16, wherein the screen is attached to the bottom of a cylinder.

20. The method according to claim 16, wherein the amount of superabsorbent polymer particles contained in the absorbent structure is predetermined and is 2.0 g.

* * * * *